US008686709B2

(12) United States Patent
Tartagni et al.

(10) Patent No.: US 8,686,709 B2
(45) Date of Patent: Apr. 1, 2014

(54) APPARATUS AND METHOD FOR COUNTING AND IDENTIFYING PARTICLES OF INTEREST IN A FLUID

(75) Inventors: Marco Tartagni, Meldola (IT); Michele Rossi, Forli (IT); Nicolò Manaresi, Bologna (IT)

(73) Assignee: Silicon Biosystems S.p.A., Bologna (IT)

( * ) Notice: Subject to any disclaimer, the term of this patent is extended or adjusted under 35 U.S.C. 154(b) by 611 days.

(21) Appl. No.: 12/866,646

(22) PCT Filed: Feb. 6, 2009

(86) PCT No.: PCT/IB2009/000211
§ 371 (c)(1),
(2), (4) Date: Nov. 15, 2010

(87) PCT Pub. No.: WO2009/098582
PCT Pub. Date: Aug. 13, 2009

(65) Prior Publication Data
US 2011/0050200 A1 Mar. 3, 2011

(30) Foreign Application Priority Data
Feb. 8, 2008 (IT) .............................. TO2008A0104

(51) Int. Cl.
*G01N 27/00* (2006.01)
(52) U.S. Cl.
USPC ........................... 324/71.4; 324/464; 324/470
(58) Field of Classification Search
None
See application file for complete search history.

(56) References Cited

U.S. PATENT DOCUMENTS

| | | | |
|---|---|---|---|
| 2,656,508 A | | 10/1953 | Coulter |
| 4,220,916 A | * | 9/1980 | Zimmermann et al. ..... 324/71.1 |
| 6,657,370 B1 | * | 12/2003 | Geusic .......................... 313/356 |
| 7,077,939 B1 | | 7/2006 | Crooks et al. |
| 2005/0118705 A1 | | 6/2005 | Rabbitt et al. |
| 2007/0159156 A1 | | 7/2007 | Hu et al. |
| 2009/0072836 A1 | * | 3/2009 | Choi et al. .................... 324/460 |

OTHER PUBLICATIONS

International Search Report and Written Opinion for corresponding international Application No. PCT/IB2009/000211, dated Jul. 8, 2009 (10 pp.).
Cheng et al., A CMOS biochip for electrical detection of DNA with an embedded current amplifier circuit, NANO/MICRO Engineered and Molecular Systems, 1st IEEE International Conference , pp. 1-6 (Jan. 1, 2006).
DeBlois et al., Counting and sizing of submicron particles by the resistive pulse technique, Rev. Sci. Inst., 41(7):909-15 (1970).

(Continued)

*Primary Examiner* — Minh N Tang
(74) *Attorney, Agent, or Firm* — Marshall, Gerstein & Borun LLP (57) ABSTRACT

Apparatus and associate method including a substrate having a first surface; a lid having a second surface; at least one spacer element interposed between the substrate and the lid so as to maintain the first and second surface spaced apart; a partition with a plurality of nanometric size through-openings interposed between the spacer element and the lid defining a first chamber a second chamber fluidically connected together through at least one of the openings; the substrate has at least one first electrode on the first surface and the lid has a second electrode, the first electrode being configured to detect an electric signal associated to the passage of one of said particles through one of the through-openings.

20 Claims, 6 Drawing Sheets

(56) References Cited

OTHER PUBLICATIONS

Han et al., Sensing protein molecules using nanofabricated pores, Appl. Phys. Lett., 88:093901-3 (2006).
Hansen et al., Microcantilever biosensors, Methods, 37:57-64 (2005).
International Preliminary Report on Patentability for corresponding International Application No. PCT/IB2009/000211, dated Aug. 10, 2010.
Kwong et al., Studies of deionisation and impedance spectroscopy, Nanostructure Instrumentation Techniques for Manufacturable Devices, Circuits and Systems: Interfaces, Interconnects, and Nanosystems, vol. 6003 (2005).
Petrossian et al., Fabrication of cyclindrical nanopores and nanopore arrays in silicon-on-insulator substrates, J. Microelectromechanical Systems, 16(6):1419-28 (2007).
Ramachandran et al., Emerging tools for real-time label-free detection of interactions on functional protein microarrays, FEBS J., 272:5412-25 (2005).
Srinivas et al., Trends in biomarker research for cancer detection, The Lancet Oncology, 2:698-704 (2001).
International Search Report and Written Opinion for corresponding International Application No. PCT/IB2009/000211, dated Jul. 8, 2009.

* cited by examiner

APPARATUS AND METHOD FOR COUNTING AND IDENTIFYING PARTICLES OF INTEREST IN A FLUID

CROSS-REFERENCE TO RELATED APPLICATIONS

This is the U.S. national phase of International Application No. PCT/IB2009/000211, filed Feb. 6, 2009, which claims the benefit of Italian patent Application No. TO2008A000104, filed Feb. 8, 2008.

FIELD OF THE ART

The present invention relates to an apparatus and a method for counting and identifying particles of interest in a fluid, possibly discriminating them from other particles of no interest.

In particular, the present invention relates to a sensor allowing to very accurately evaluate the concentration of particles of interest in a fluid, on the basis of the interfacing of microelectronic technologies with a nanoporous partition, and to a respective method for quantifying on the basis of the individual count thereof.

STATE OF THE ART

In the field of both academic and industrial scientific research, there have been in recent years considerable efforts to develop biosensors allowing to very accurately evaluate the concentration of particles of interest. In particular, the need has arisen over the years for devices for the low-cost determination of biomarkers allowing to distinguish among different kinds of molecules. The possibility of very accurately determining properties and concentrations of biomolecules of interest by means of simple, miniaturised and low-cost systems is an increasingly felt need in medical practice, from preventive diagnostics to therapeutics. In particular, this need applies to the study of biomarkers (biological markers) for the preventive diagnosis of various diseases, with special reference to tumours. The most recent interest in diagnostic systems for detecting biomarkers in-vivo in humans and animals should especially be noted.

Biomarkers are molecular indicators of the progress of a disease and are studied, with particular reference to the prevention of tumours, before the symptomatic onset of the disease itself (P. Srinivas et al., The Lancet Oncology vol. 2, pp. 698-704, 2001).

Especially interesting biomarkers are based on the analysis of protein profiles of cell content (protein fingerprint), useful to verify the stage and evolution of cell signalling and, specifically, scientific research has in recent years focussed on the study of protein profiles by means of quantitative analyses at low concentrations (on the order of femtomoles), which allow to detect specific biomarkers.

In recent years, different technologies have been developed in the field of study of protein expression (proteomics).

Some of these use molecular labels for detecting biomarkers, others (label-free technologies) require no molecular labels as it is known (see Ramachandran et al., The FEBS Journal, 272, pp. 5412-5425, 2005) that labels considerably interfere with the ability of proteins to interact with other small and non-proteic molecules (lipids, nucleic acids, etc). Furthermore, the use of molecular labels fails in one of the most important frontiers of diagnostic research: protein-protein interaction.

In particular for detecting single molecular events, in recent years technologies alternative to those already commercially available have been scientifically studied and, specifically, scientific research has increasingly focused on the study of nanopore technology.

Nanopore technology, which was developed in the nineties with the aim of sequencing single DNA strands, is very often referred to as nano-Coulter as it is based on a device designated Coulter-Counter, which is disclosed in U.S. Pat. No. 2,656,508 and has also been pioneeringly tested on nanometric polystyrene particles in the seventies (R. W. DeBlois et al. in Rev. Sci. Inst., vol. 41, n. 7, 909-915, 1970).

The possibility of generating artificial nanopores made of organic or inorganic material has recently been investigated. Furthermore, some publications (A. Han et al. Appl. Phys. Lett., 88, 93901-93903, 2006) have recently shown that nano-Coulters may be effectively used not only for DNA strands but also for single biological macromolecules which do not aggregate in strands.

Figure 1:
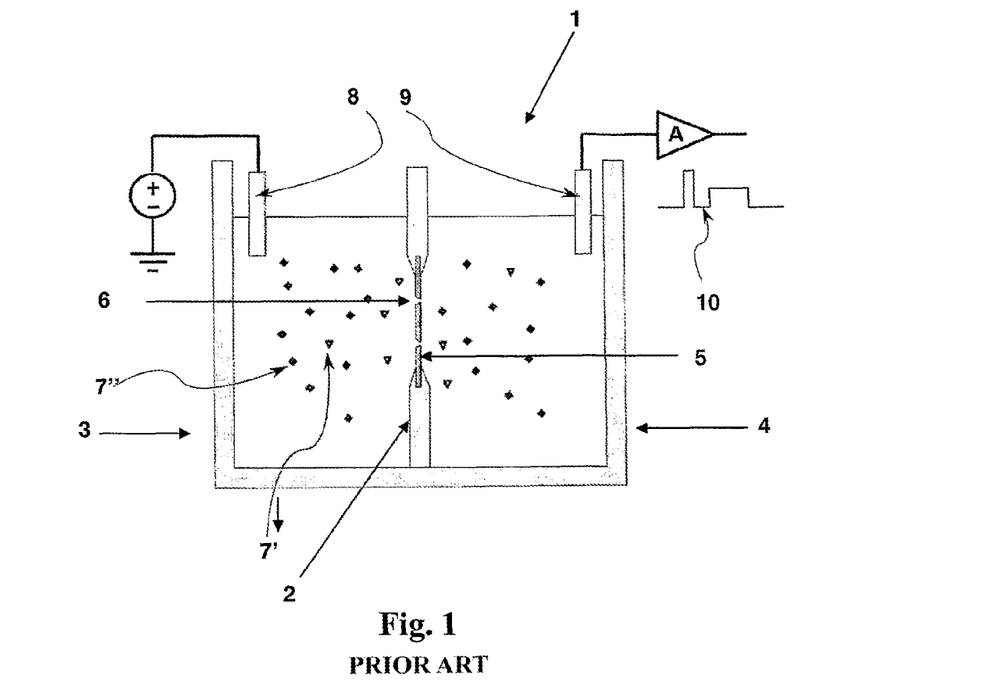
FIG. 1 is a diagrammatic representation of an experimental system according to the known state of the art for counting molecules by means of a process of the nano-Coulter type.
Figure 2:
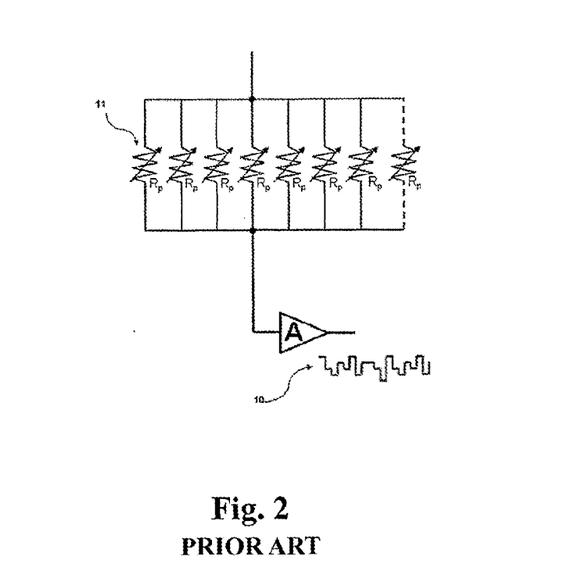
FIG. 2 shows a diagrammatic representation of the equivalent electronic circuit of the nano-Coulter system of FIG. 1 and the qualitative trend of the corresponding output signal following ion current in the nanopores.

FIG. 1 shows a known system 1 for counting molecules of the nano-Coulter type which is part of the known art. This system is based on the use of a partition 2 as a separation wall between two tanks 3, 4 adapted to contain a liquid. Partition 2 comprises a central nanoporous portion 5 consisting of a membrane which may be made of different materials, such as silicon, silicon nitride or polymeric compounds having perforations 6, or nanopores, having a diameter of 10-100 nm and a depth of the same order of magnitude. In use, tanks 3 and 4 are filled with liquid (for instance KCl aqueous solution with the addition of Tris) containing a plurality of macromolecules 7 of the 7' and 7" type which may even be different from one another (biological molecules with a diameter varying from 2 to 30 nm) having an electrical charge (most proteins and DNA fragments have some positive or negative net electrical charge). When a first and second electrode 8, 9—each positioned in a respective tank 3, 4—are placed in contact with the liquid in the tanks, a potential difference occurs between the two tanks so as to push ions (K+, Cl−, etc.) and macromolecules 7 through nanopores 6 of nanoporous portion 5. As ions are generally one order of magnitude smaller with respect to that of macromolecules 7, the passage through nanopores generates a ion current, detectable by current amplifier A. The passage of macromolecules 7 through nanopores 6 instead determines a variation in the ion current determined by the partial obstruction of the conductive path they determine. This variation may be represented by the variation of a resistance Rp in the circuit as shown in FIG. 2. The passage of single molecules 7 through nanopores 6 is therefore detectable by the presence of modulation spikes of the overall ion current and is recorded through output signal 10 of signal amplifier A.

The set forth system therefore offers a technology allowing to determine the concentration of chemical substances by counting the molecular events analysed by electrical signals. However the cited methodology has a series of drawbacks. As shown in FIG. 2, the overall signal consists of the sum of different signals added to one another. The action of obstructing the ion current in nanopore 6 by means of molecules 7 is indeed comparable to that of varying a variable resistance 11 in an electric circuit. In the frequent case in which more than one nanopore 6 is present in the partition, overall output signal 10 results hard to interpret as it is the sum of different current contributions in parallel. Finally, the system is not specific for only one class of molecules as each macromolecule 7, 7' that manages to pass through nanopore 6 generates a respective spike which may not singularly be detected in overall signal 10.

To overcome these drawbacks, US2007/0159156 discloses a nano-Coulter device in which the nanoporous partition has, at each pore, a respective control electrode, as also suggested in U.S. Pat. No. 5,376,878, which activates or inactivates the electric signal coming from the pore, in order to detect single current spikes in the overall signal. This device although requires additional electric connections and microfluidic systems in the nanoporous membrane which render the device extremely complicated.

A further device of the type for counting microparticles is that disclosed in U.S. Pat. No. 7,279,883. This device, made by processing a polymeric material and exploiting microfluidic system technology, comprises a substrate that has electrodes on which a lid made of elastomeric material is placed. The tanks containing liquid consist of capillary microfluidic channels and the pores are obtained as narrowings of the capillary channel at projections or recesses obtained in the substrate or in the lid.

This device requires a very accurate machining for obtaining pores with a predetermined diameter and furthermore does not allow a use flexibility with different kinds of molecules. It is also very difficult to obtain nanometric pores by this approach, due to the impossibility to control the tolerances of the polymeric structures used to form the capillary channel. Given the particular mode of implementing the geometry of the device, the suggested approach is not suitable for large matrix size and offers no methodology for counting molecules of a specific species.

In other terms, the above disclosed systems do not allow in most cases to discriminate particles of interest and, where possible, the discrimination occurs by means of the recognition of a signal profile, which represents an extremely critical methodology.

DISCLOSURE OF INVENTION

It is the object of the present invention to solve the existing problems by means of a method and an apparatus allowing to count the number of particles of a determined species in a simple manner and without the aid of sophisticated instrumentation.

It is also the object of the present invention to solve the existing problems by means of a method and an apparatus allowing to very precisely identify the concentration of particles of a determined species in the presence of other different particles in a simple manner and without the aid of sophisticated instrumentation.

In particular, according to the present invention an apparatus is provided, which allows to count the particles within a sample, possible having discriminated those of interest from the others on the basis of their interaction with appropriate specific receptors. In particular, an apparatus according to claim 1 is provided.

According to a further aspect of the present invention, a method is also provided for counting particles in a sample, in which the particles may possibly previously be discriminated from particles of no interest on the basis of their interaction with appropriate specific receptors. In particular, a method according to claim 18 is provided.

BRIEF DESCRIPTION OF THE DRAWINGS

Further advantages and features of the present invention will result apparent from the following disclosure of a preferred embodiment thereof, provided by way of mere non-limitative example and with reference to the accompanying figures, in which.

DESCRIPTION OF THE INVENTION

According to the invention, an apparatus and a method are provided allowing to perform a quantification of the particles both in the absence and in the presence of (fluorescent, radioisotopic) labels or (polymeric or magnetic) microbeads currently used for these purposes. The apparatus is based on the coupling of nanoporous partitions with intelligent electronic substrates and is applied in the field of diagnostics and therapeutics. In virtue of the reading system which may be miniaturised considerably, the apparatus and method set forth are among the very few examples of technology with the potential of being used in applications in-vivo, as well as for conventional applications in-vitro. In this latter case, in virtue of the structural simplicity, the device could be implemented in low-cost systems of the disposable type.

Figure 5:
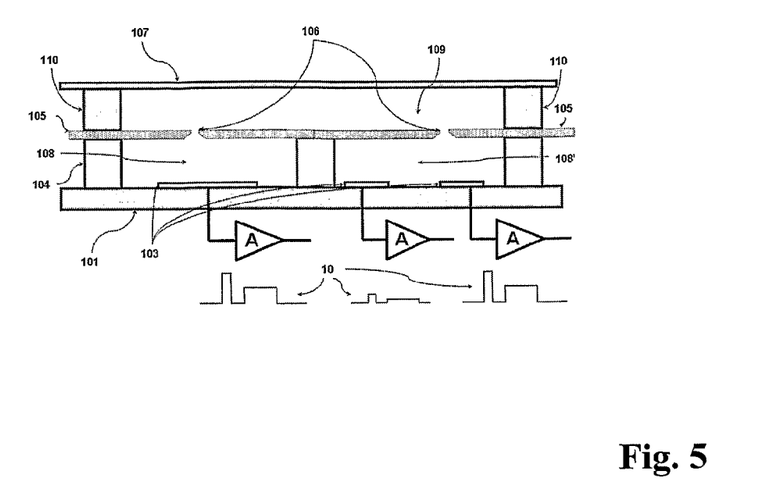
FIG. 5 shows a diagrammatic representation of a side section view of an embodiment of the device according to the invention, together with the qualitative trend of the output signal of the corresponding electronic circuit.

The present invention therefore provides a method allowing to increase the discriminability of single molecular events the surface of the nanoporous partition being partitioned in subdomains, each of which is associated to at least one electrode 103 connected to an electric signal amplifier A which determines single impulses coming from the subdomains, as highlighted for instance in FIG. 5. In this manner, the count of the single events coming from each single subdomain may be summed altogether so as to deduce the overall concentration of the particles of interest in the sample with a great statistic confidence.

Apparatus-A (Main Configuration)

Figure 3:
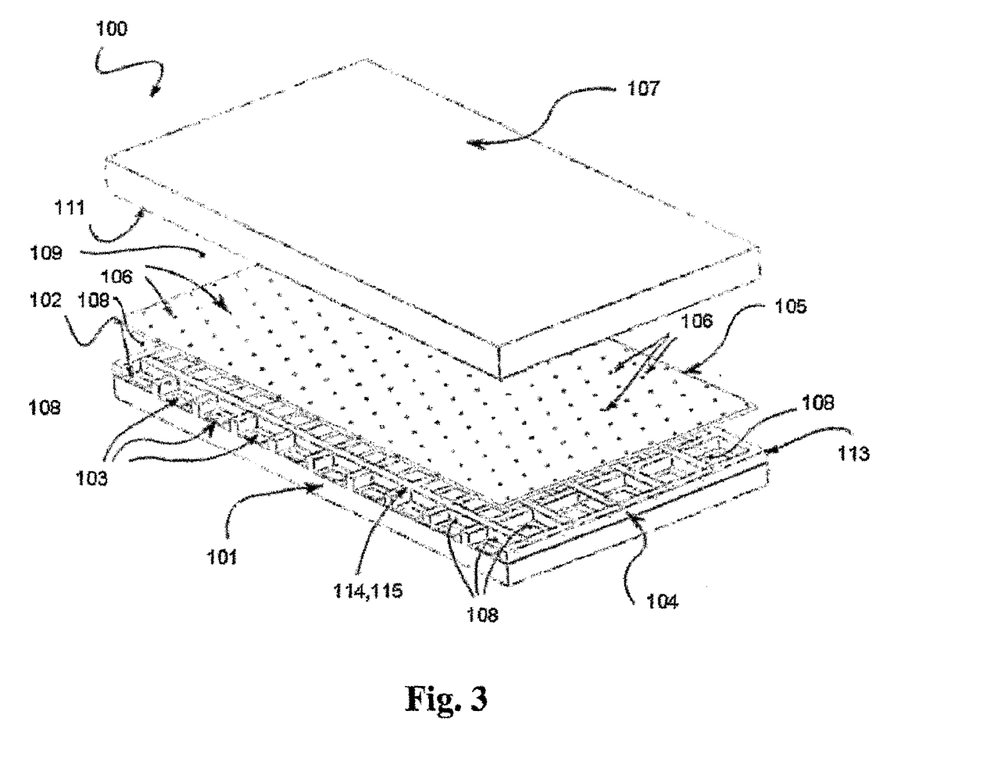
FIG. 3 is a diagrammatic representation of an exploded perspective view of the device according to the present invention.
Figure 4:
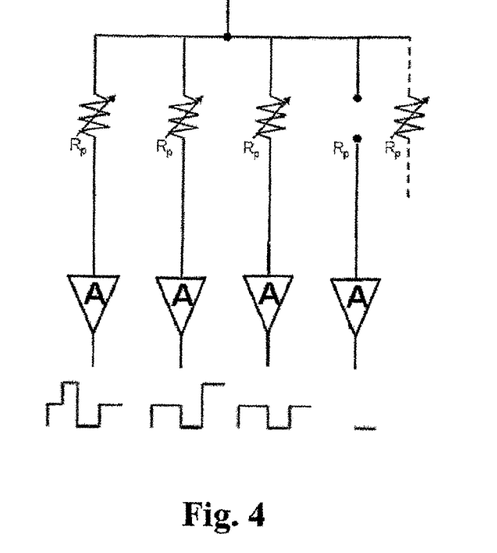
FIG. 4 shows a diagrammatic representation of the equivalent electronic circuit of the system of FIG. 3 and the qualitative trend of the corresponding output signal following ion current in the nanopores.

To achieve the above disclosed functionalities, an apparatus of the type shown in FIG. 3 is provided according to the present invention.

According to an embodiment of the invention, the apparatus indicated as a whole by 100, consists of: a substrate 101 made of silicon or another material (for instance glass), on a first surface 102 of which one or more electrodes 103 are obtained (in the case of a plurality of first electrodes 103, these are arranged according to a mono- or bi-dimensional array and are electrically and geometrically separated from one another, as will be disclosed in greater detail hereinafter); a lid 107 having a second surface 111 facing first surface 102, where lid 107 also serves as single second electrode (or as an alternative on which second surface 111 a single second electrode 107' is obtained); a spacer element 104; a partition 105 made from materials (such as for instance silicon, silicon oxide, silicon nitride, various polymers, etc.) allowing to be micro- or nano-machined to obtain a plurality of through-openings 106 having nanometric size therein.

Partition 105 is interposed between the at least one spacer element 104 and lid 107 so as to define at least one first chamber 109 between the partition and the lid and at least one second chamber 108 between partition 105 and substrate 101. The first and the second chamber 108, 109 are fluidically connected to one another through at least one of openings 106.

Spacer element 104 comprises a peripheral element 113 which laterally defines second chamber 108.

The number of electrodes 103 obtained on surface 102 and comprised within the portion of surface 102 delimited by peripheral element 113 is greater or equivalent to the number of openings 106 in the portion of partition 105 correspondingly delimited by peripheral element 113. The correspondence does not require a precise alignment of structures 101 and 105.

According to the invention, each electrode 103 is configured so as to detect a variation of an electric magnitude associated to the passage of a particle of interest 7" within a population which also comprises particles 7, 7" through a through-opening 106 of partition 105, having appropriately associated each single electrode 103, or a set of electrodes 103, to a pore 106 of partition 105.

As the electric signal detected by means of electrodes 103 is a direct function of the number of particles present in the fluid contained in the apparatus according to the invention which flows through partition 105, by means of an appropriate processing of the signal itself, it is possible to correlate it to a characteristic property of the fluid itself, such as for instance the concentration of the species of interest. As a matter a fact, the apparatus allows to effectively and precisely count the particles contained in a known volume of the tested fluid.

It should be noted that in the case in which the "subdomain" has a plurality of electrodes and a plurality of nanopores, such a configuration consisting in associating a respective electrode to each nanopore, is achieved by selecting the electrodes recording the maximum intensity signal among all the electrodes of the "subdomain". Since the maximum intensity signal is detected by the electrode nearest to the nanopore, a nanopore may be associated to the nearest electrode by means of the same electric signal used for the count.

Lid 107 instead has a second electrode having a second surface 111 opposite to partition 105 and preferably extending over an area substantially equivalent to that of the array of electrodes 103. It is also possible to have a single top electrode having the same size as one of the arrays of electrodes 103 on the lid, or even an array of electrodes 107 substantially equivalent to that formed in the substrate by electrodes 103.

It should however be noted that, in the case in which lid 107 houses a plurality of electrodes, the device as a whole actually results from the juxtaposition of a plurality of subdevices of the previously described basic type, in each of which a single top electrode is opposed to a corresponding electrode 103, or to a corresponding plurality of electrodes 103 arranged according to an array.

Furthermore, according to the invention, the spacer element comprises means 114 for the separation of second chamber 108 in a plurality of microchambers 108'.

In a first embodiment of the invention, such separation means 114 consist of a grid 115, each mesh of which physically delimits each single electrode 103 of the plurality of electrodes arranged as an array from the adjacent electrodes, substantially defining a corresponding plurality of first chambers 108' each comprising a single electrode 103.

In a second embodiment, separation means 114 consist of a grid 115' (not shown) the meshes of which have a size larger that those of a single electrode 103, and more in particular in a grid 115' each mesh of which physically delimits a subset of first electrodes 103 from the adjacent electrodes, substantially defining a plurality of chambers 108' each comprising a corresponding subset of electrodes 103. Also in this case, according to the invention, the condition occurs in which the number of electrodes 103 in each chamber defined by a single mesh of grid 115' is greater or equivalent to the number of openings 106 in the portion of partition 105 delimited in turn by the same mesh of grid 115'.

The components which form apparatus 100 are stacked in close contact with one another (or even stacked). The geometrical arrangement of openings (also nanopores) 106 with respect to the surface of partition 105 may substantially be any, as the matrix structure allows, during processing of the output signal from the system, to use the redundancy of the data to compensate for possible statistical distributions of the arrangement of nanopores 106.

FIG. 5 diagrammatically represents the cross section of the structure of apparatus 100 of FIG. 3, of which only the case in which a chamber 108 containing a single electrode 103 and that of a chamber 108' which contains two electrodes 103 are shown. The apparatus comprises a spacer 110 which is positioned at the edges of the structure and interposed between partition 105 and lid 107. Its use, however, is not always required, as the nanometric size of the single constitutive elements of the device is immeasurably smaller with respect to mechanical tolerances existing among the various structures. This means that common chamber 109 is substantially identified even if lid 107 and partition 105 are placed in use directly in (apparently) close contact with one another.

Figure 6:
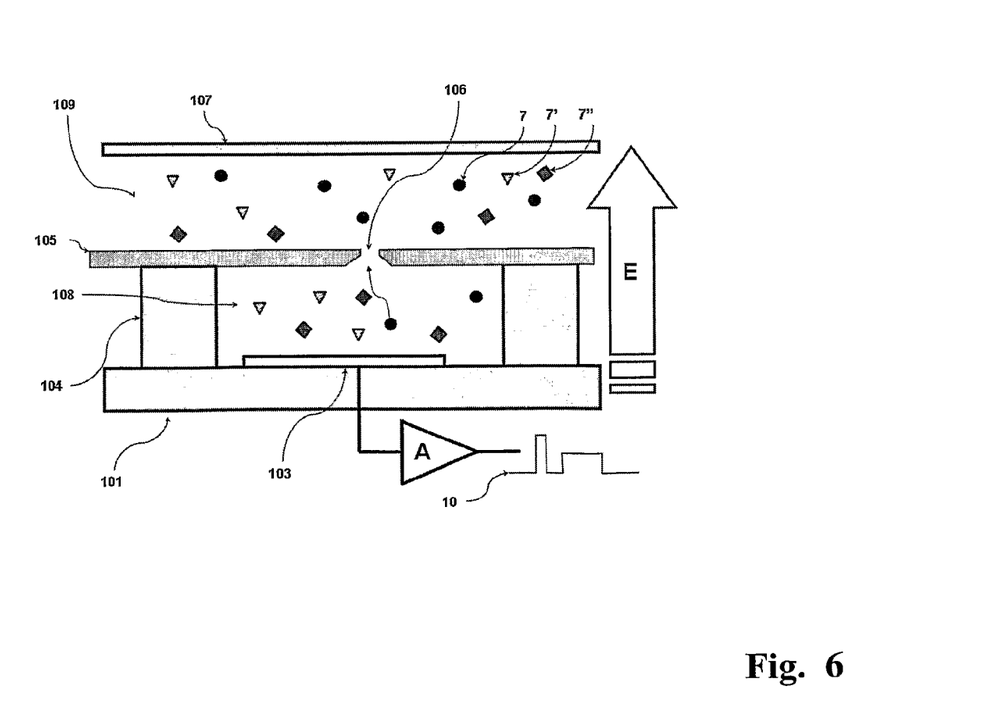
FIG. 6 shows a detailed view of a section of the device in FIG. 5 in use according to the method of the invention.

FIG. 6 shows a further cross section view of apparatus 100 of FIG. 3 at a single electrode 103, in which different species of particles are identified within corresponding chamber 108. Hereinafter, the term "particles" (7, 7', 7") indicates any micro- or nano-scopic element even of biological origin, and preferably electrically charged, such as, for instance: molecular elements or agglomerates, proteins, protein agglomerates, viruses, prions, organelles, bacteria and cells. Furthermore, considering the possibility of obtaining nanopores with a diameter on the order of 1.5-3 nm, even the identification of strands of DNA, ssDNA or cDNA in solution may be carried out by this apparatus.

Device 100 may be assembled by using parts made independently by different manufacturers.

According to a possible embodiment, there may be used: i) a silicon substrate 101 manufactured according to the common procedures of microelectronic manufacturing, surface 102 of which is depassivated by means of conventional procedures of selective etching, and in which the matrix of electrodes 103 is made with the most external layers of metallisation; ii) a separation grid 104 made on surface 102 of substrate 101 with conventional procedures of selective polymeric deposition (for instance by using polydimethylsiloxane, PDMS or SU8); iii) a partition 105 made by means of known nanomanufacturing procedures.

The above said parts are stacked one on the other as shown in FIG. 3 by using lid 107 as outermost end part, which is placed in its seat shortly before the actual use, after having ensured diffusion of the solution to be analysed in the microchambers avoiding the presence or formation of air bubbles. No self-alignment procedure among single elements is required.

In particular, nanoporous partition 105 is commercially available from companies industrially producing nanopores. By way of example, Applied NanoStructures provides devices made of silicon nitride ($Si_3N_4$) or silicon dioxide ($SiO_2$) with 200 nm-thick nanoporous partitions which have pores with a diameter from 200 nm to 20 nm. These chips are funnel-shaped at each pore, in the sense that the partition has a thinner portion (200 nm) at each pore and a thicker portion (300 nm), in order to ensure the hardness of the structure to be handled and at the same time maintain a capacity of the partition to ensure a good quality of the signal to acquire, as will be explained more in detail hereinafter.

Each electrode 103 of substrate 101 has a rectangular, square, rhomboidal or circular section, but preferably a square section for structural simplicity, and has a size in the range between 55 nm and 600 μm.

Each mesh of grid 115 is similarly rectangular, square, rhomboidal or circular, but preferably square for structural simplicity, and has a size in the range between 5 μm and 1 mm.

Lid 107 has a thickness in the range between 5 μm and 1 mm and its surface 111 has at least one rectangular, square, rhomboidal or circular electrode, having a size that depends on the number of electrodes 103 included within the corresponding chamber (108, 108'). In the case of a single electrode on the lid, the size of the electrode on surface 111 is in the range between 10 μm a 10 mm. The electrode is electrically connected with the input of an electric signal amplifier A that allows to determine the variation of signal 10 induced by the flow of particles in nanopores 106.

The overall size of the substrate with electrodes and grid are therefore in the range from 100 μm to 10 mm and there are contacts (as many as the electrodes) on the external part of the substrate in order to measure the variation of impedance of the single nanopore.

It should be noted that all these sizes may be scaled on the basis of the size of the nanoporous membrane, therefore on the basis of the number of nanopores involved and accordingly to that of the electrodes in the substrate. Furthermore, the size depends on the type of molecule of interest and application involved.

Amplifier A may detect an electric signal in each electrode i.e.: a current signal (to detect the current, the potential between the electrodes of the substrate and that/those of the lid is set); a voltage signal (to detect the voltage the current is kept constant), a signal expressing the charge stored in electrode 103.

In use, the operator takes the substrate with the electrodes and the grid with tweezers, he/she washes it, he/she dips the support with electrodes and grid in the solution in which there are molecules to be analysed, he/she takes the previously cut nanoporous membrane (it may already be commercially available in the appropriate size), he/she takes the lid (with tweezers) and dips it in the solution to be analysed, he/she overlaps the whole by stacking it. In order to maintain the three parts stacked, it will be apparent to the person skilled in the art that clips or mechanical or reversible chemical bonds may be used among the parts.

Subsequently, the operator positions the above said components in a square support (for instance made of silicon) having a size from 100 μm and 15 mm that has a housing provided with contacts which couple to contacts of the substrate itself.

In an alternative configuration the overall system 100 may be preassembled by arranging around chamber 109, as a spacer element, a gasket 110 and fluidic input and output systems (not shown in the Figures). After having eliminated any air residue by means of methods of the state of the art (ultrasonication with vacuum pump, injection of high $CO_2$ solutions, etc.) the sample to analyse is flowed (for instance by means of a microfluidic connection) in chamber 109 until the main configuration is achieved.

As already mentioned, the application of a potential difference between electrodes 103 and lid 107, or electrode 107' obtained on surface 111 of the lid, determines an electric field E that pushes ions dissolved in the fluid and the charged particles suspended in the solution from chambers 108, 108' to common chamber 109 (or vice versa) through nanopores 106. The passage of the particles may be identified from the current signal amplified by each amplifier A possibly and conveniently implemented in the same substrate 101 underlying each electrode 103, in the case in which for instance this substrate 101 consists of crystalline silicon.

By way of example, the following configuration, which relates to negatively charged particles, may be used: each electrode 103 is connected to a current amplifier A the input of which is virtually grounded; the application of a positive potential difference of a few hundreds of mV to lid 107 induces an electric field E that causes particles 7 to move vertically upwards through nanopores 106.

It should be noted that overall output signal 10 may easily be reconstructed as the sum of signals recorded in parallel by each electrode. For instance, if a signal that may be traced back to an impulse corresponds to each particle passing through pore 106, the sum of the impulses corresponding to all of the electrodes is indicative of the number of particles in a chamber and passing through the partition, i.e. indicative of the concentration. The main advantages of apparatus 100 may be summarized as follows:

1. considerable increase of the amount of data made available to a single experiment;
2. drastic increase of the signal-disturbance ratio due to the miniaturisation of chambers 108, 109 and of electrodes 103 and to the proximity of amplifier A possibly implementable in the same substrate;
3. easy assembly, as the main components of the structure may be manufactured independently by the manufacturers and/or subcontractors according to the state of the art and only subsequently stacked in a simple stack structure;
4. no need for micromechanical positioning or alignment between the different structures which form the apparatus;
5. very good versatility of the system in the potential for miniaturisation, allowing in-vivo applications.

In particular, the current signal to be acquired depends both on the properties of the molecule to be detected, and on nanoporous partition 105. Considering a target molecule having a diameter d and using a nanopore 106 (for which an internal cylindrical geometry may approximately be assumed) having diameter D and length (substantially equivalent to the local thickness of partition 105) L, the variables determining the electrical behaviour may be reduced to two, and accordingly the quality of the signal to be detected and analysed: the two ratios d/D and D/L. The relation that connects the variation corresponding to the resistance of the pore following occlusion by target molecules, and therefore also the variation of the amplitude of the current signal, is that described by equation (1)

$$\frac{\delta R_p}{R_p} = \frac{D}{L}\left[\frac{\arcsen\left(\frac{d}{D}\right)}{\sqrt{1-\left(\frac{d}{D}\right)^2}} - \frac{d}{D}\right] \quad (1)$$

The ratio d/D is the one most notably affecting the signal-noise ratio; nevertheless, when the value of this ratio approaches 1, the probability of the pore being clogged increases considerably and accordingly the impossibility of the molecules passing therethrough. This leads in practice to the impossibility of using the sensor.

The second ratio that adjusts the behaviour and the quality of the signal to be detected is less relevant on the signal-noise ratio, but implies a greater freedom in the selection of the size of the nanopores. Furthermore, this second ratio is completely independent of the nature of the target molecules, whereas it is related to the kind of material used as a support for the formation of the pores and its physical properties (for instance malleability). Keeping in mind the considerations previously set forth and having set a certain ratio d/D, to increase the ratio D/L as much as possible, the thinnest possible nanoporous partitions are to be obtained; the (downward) limit in length L of the pore is only determined by the physical resistance of the nanoporous membrane and by other capacitive aspects thereof, which could create problems relating to the actual band detectable by the sensor. For this reason, funnel-shaped structures with a thicker area (on the order of μm), that serves both as a support and to decrease the overall capacity of the porous membrane, and a very thin "sensing area" (on the order of nm) comprising the pore are often generated; the latter must also have an extremely limited area, in order to produce an increase of the capacity of the membrane which is as limited as possible.

Figure 7:
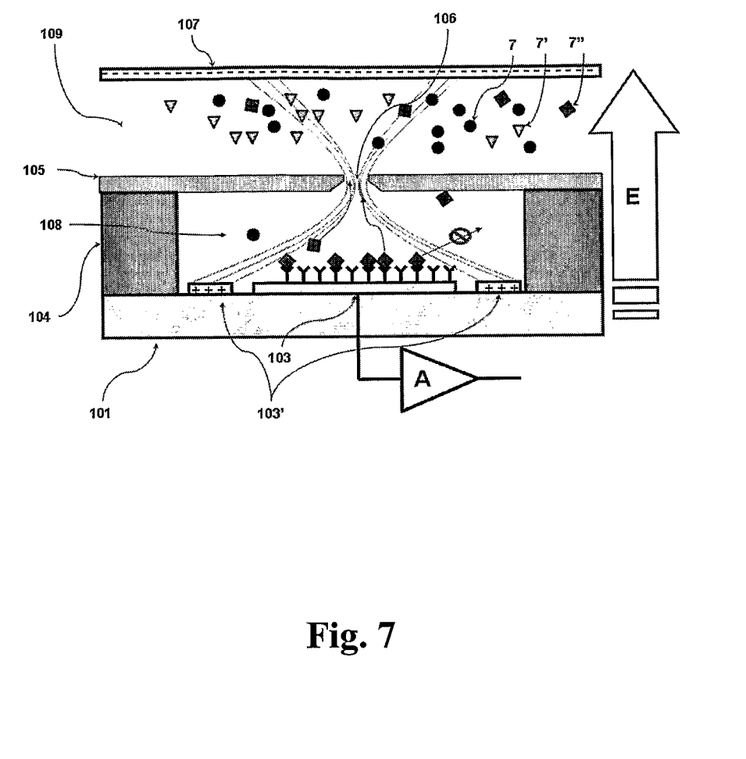
FIG. 7 shows consecutive steps of the method according to the invention through corresponding detailed views of a section of the device of FIG. 5.

With reference to the device of FIGS. 3 and 5, which represent a first basic embodiment of the invention, it should be specified that separation grid 104 is required to space partition 105 from substrate 101, but it is not indispensable for the electric separation of single chambers 108'. By using an appropriate focusing of the electric field, the particles may indeed be pushed from underlying electrode 103 through overhanging nanopores 106 without the particles themselves being dispersed towards the nanopores corresponding to other electrodes 103 (FIG. 7). This is made possible by having recourse to focusing electrodes 103', not connected to amplifiers A and placed immediately near electrodes 103 (for instance in a "guard ring" configuration, i.e. a circular crown about the electrode of interest as shown in FIG. 7) which repel the generic particles (possibly positively/negatively charged) by means of a potential barrier generated by placing electrodes 103' at a potential difference slightly positive/negative with respect to the value of the potential of electrode 103. This allows to focus the electric field in nanopores 106 directly overhanging electrode 103 (FIG. 7).

The use of focusing electrodes 103' further results especially beneficial in the above cited case in which there are multiple electrodes 103 for each chamber 108', as it allows to direct the particles of interest towards a specific through-opening or nanopore 106 univocally associated to each of electrodes 103 of the chamber. A specific electrode 103 or a specific subset of all of electrodes 103 of the array may indeed univocally be associated to a specific nanopore in use.

The solution set forth in the previous paragraphs allows to very precisely count single particles without however discriminating a species with respect to all of the others, a functionality which is instead very interesting in all fields of diagnostics and sensoristics in general.

A method and an apparatus will be disclosed hereinafter for counting and detecting different species of particles.

As shown in FIG. 7, surface 102 is appropriately "functionalised" with respect to the molecular species of interest, i.e. following the known art, molecules R (receptors such as for instance antibodies, aptamers) are deposited on surface 102 and can interact by means of non covalent chemical bonds with particles of interest. This functionalisation may be carried out on the different elements of surface 102, i.e. both directly on substrate 101, and on electrodes 103 that are obtained thereon. In the case in which ssDNA or cDNA are to be analysed, it will be sufficient to functionalised the surface with (random or specific and known) oligonucleotide sequences (instead of receptors R), similarly to the techniques used for the formation of DNA microarrays.

Figure 8:
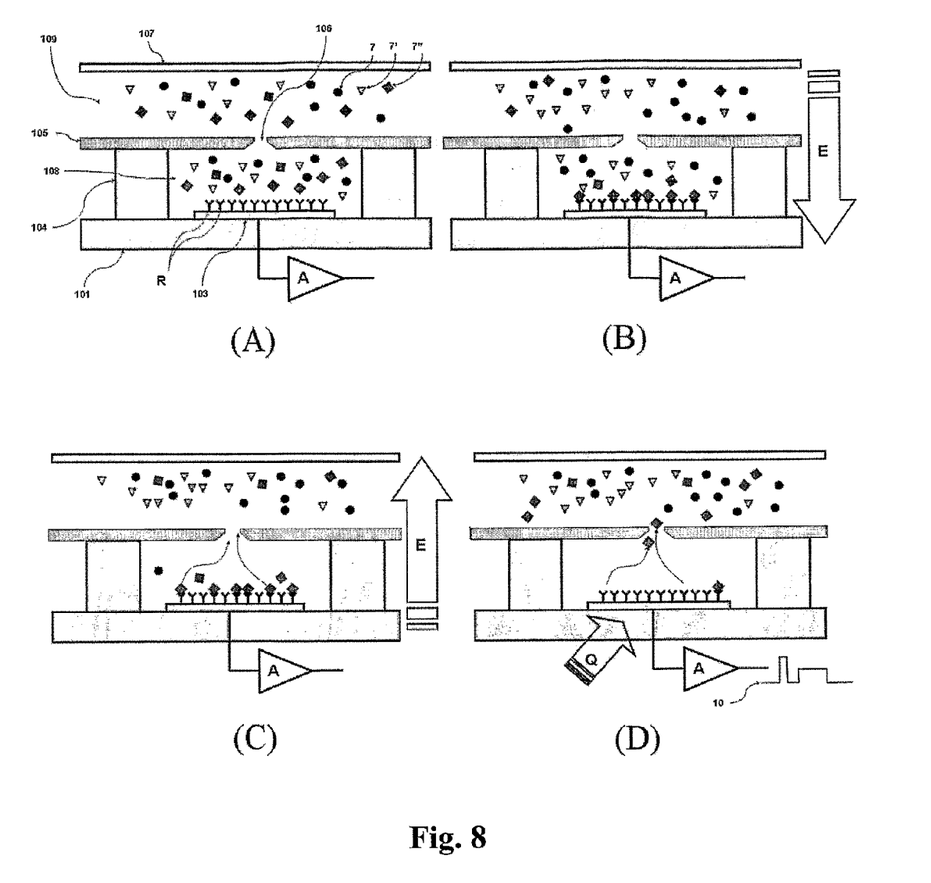
FIG. 8 shows a further detailed view of a section of the device in FIG. 5 in use according to a further embodiment of the method of the invention.

For the sake of clarity, in the particular case shown in FIG. 8A, the surface of electrode 103 is functionalised with respect to the molecule of interest indicated with the quadrangular profile (7"). The chemical species in the top chamber 109 tend to naturally diffuse through nanopores 106 in the various underlying microchambers or cells 108. As shown in FIG. 8B, promoting such a diffusion by means of the application of a potential difference such as to create an electrical field (indicated in the Figure with arrow E) pushing the macromolecules towards electrode 103 could be effective (although not necessary). In the course of time, particles of interest 7" tend to bind to the surface of electrode 103 according to the laws of chemical equilibrium. As shown in FIG. 8C, the application of an electric field E having an opposite direction, will tend to take back other particles 7, 7' in top compartment 109, with the exception of those of interest 7", as they are bound to functionalised electrode 103. At this point, the application of an increase in the temperature, by means of thermal shock, at molecules R (or at the oligonucleotides if DNA strands are considered), promotes the release of particles of interest 7" which are always drawn by the same electric field E towards common chamber 109, as shown in FIG. 8D.

The detected electric signal is a direct function of the number of particles which pass through partition 105, therefore it may be correlated by means of an appropriate processing thereof to a typical feature of the fluid itself, such as for instance the concentration of the species of interest.

It should be noted that the recording of the passage of the particles of interest in the latter step allows an accurate evaluation of the concentration thereof without the aid of molecular labels. It should be noted that the generation of a thermal shock of a few dozens of degrees centigrade is a relatively easy procedure to perform and may be controlled, as in the known art, by using structures integrated in the microelectronic substrate allowing to generate and measure temperatures very precisely.

To support the concept, in the case of molecules, the concentrations may be correlated by means of the law of mass action. If [A] is the concentration of the receptors and [B] is the concentration of the molecules of interest, that is to be determined, and [AB] is the concentration of the molecules of interest bound to the receptors, then according to the law of mass action:

$$\frac{[AB]}{[A][B]} = K(T) = e^{-\frac{\Delta G^0}{RT}} \quad (2)$$

where K (T) (expressed as 1/mol) is a constant exponentially depending on the temperature and $\Delta G_0$ (expressed in kcals/mol) is the bond energy of the reaction between ligand and receptor. As is known in the literature and in experimental biochemistry, non-covalent bond energies (for example the hydrogen bond) vary from a few kcal/moles to a few dozens of kcal/moles. By substituting these values in equation (2) for values of bond energy equivalent to $\Delta G_0$: 4 kcal/mol, 10 kcal/mol and 25 kcal/mol for temperatures of 10° C. and 70° C. we respectively obtain the ratios of the dissociation constants equivalent to:

$$\frac{K(10°\ C.)}{K(70°\ C.)} @ \left(4\ \frac{kcal}{mol}\right) = 3.5;$$

$$\frac{K(10°\ C.)}{K(70°\ C.)} @ \left(10\ \frac{kcal}{mol}\right) = 22.4;$$

$$\frac{K(10°\ C.)}{K(70°\ C.)} @ \left(25\ \frac{kcal}{mol}\right) = 2385$$

This means that the ratio between the dissociation constants may vary from a factor 3 to several orders of magnitude if the temperature rises by about 60° C. In other terms, the ratio between the concentration of free target molecules at 10° C. and free molecules at 70° C. increases by orders of magnitude for typical values of bond energy. Another important observation is that the imbalance increases as the bond strength increases, which is in most cases related to the size of the target molecule with the respective receptor.

The two most commonly used procedures to functionalise surfaces are the use of silanes or thiols, which can establish covalent bonds respectively with silicon or gold surfaces by the self-assembly of monolayers (SAM, Self Assembled Monolayer) of biological structures. These biological structures may directly be antibodies, aptamers or protein or molecular linkers which serve as a bridge between the substrate and the antibody or the aptamer.

An example of antigen/antibody pair may be the use of RAH-PSA (antibody) specific for the PSA antigen, a biomarker for prostate cancer. The antibody may be immobilised on a gold surface by using DTSSP, a protein linker which can bind on one side to gold and on the other to amine groups of the antibody (see "Microcantilever biosensors" Hansen M. K., Thundat T., Methods, 37, 57-64, 2005).

What has just been disclosed is only an example and many kinds of antibody/antigen complexes may be used on the basis of the application of interest. It is also apparent for the person skilled in the art that there may be different embodiments of the method, which differ from the previously disclosed procedure only for practical aspects substantially known by the person skilled in the art, without however departing from the scope of protection defined by the claims.

According to an embodiment of the method of the invention, the release of particles of interest 7" from underlying surface 102 may be promoted not by the application of a thermal shock, but by using the activation of an appropriate light radiation (for instance having a wavelength corresponding to ultraviolet rays) which can weaken the bonds between molecules of interest 7" and receptors R. For this purpose, a transparent support substrate 101 for the array as well as transparent electrodes 103 may be used, for instance using a process based on the use of "Indium Tin Oxide" (ITO) commonly used to make conductive paths on a glass substrate. As far as the emission is concerned, it is sufficient to place a generic light source (not shown) having an appropriate photonic energy immediately below substrate 101 and activate it at the appropriate moment in the course of the application of the method, as previously disclosed.

It is also apparent that it is possible to perform a diversified functionalisation, i.e. deposit different receptors R, R', R" each respectively conceived for different molecules 7, 7' and 7" (that of interest) on subdomains of the array of electrodes 103 of the device. The same considerations may be made for different oligonucleotide sequences, which can hybridise different sequences of DNA.

For this purpose, chemical agents which can functionalise the surface of respective electrodes 103 and/or adjacent surfaces for different particles of interest will be dispensed in drops by means of a dispensing machine or microspotter in each cell 108 or on sets of cells forming subsets of the array. After the sample to be analysed has been introduced and device 100 has subsequently been closed by means of partition 105 and by lid 107 as already disclosed in detail, the activation of a thermal gradient or optical irradiation at the basis of structure 101 allows, as already shown, to weaken the bonds created between the particles and the receptors, so as to allow the passage of the particles, with the possible aid of electric field E, through nanopores 106 of respective cells 108.

By operating in this way, the concentration of different molecular species contained together in the same sample may be evaluated and identified at the same time without the aid of any kind of labels. This potential is crucial to perform, for instance, a protein profiling of the sample as already set forth previously.

In the case in which the nanotechnology used to form nanoporous partition 105 does not allow to obtain nanopores with a small enough diameter to allow to discriminate single particles or molecular aggregates, calibrated polystyrene microbeads, which are widely available commercially, may in any case be used. According to this procedure, microbeads made of polystyrene or other materials are functionalised, as in the known art, for molecules or molecular aggregates 7, 7', 7" by means of specific receptors R. Microbeads interact with the particles of interest by forming complex agglomerates. These agglomerates may in turn interact with functionalised surface 102, by binding to the latter. Also in this case, different alternatives which may be used are known in the art (for instance receptors of the electrode different from those of the microbeads and variously specific for different receptor sites of the particle of interest). Once the weak bond is obtained between the microbeads and functionalised bottom surface 102, it is in any case sufficient to activate a weak electric field E or flow so as to clean microchamber 108 of all the particles which are of no interest, as they are not bound, by means of microbeads, to the functionalised surface. By maintaining the same weak electric field, a thermal flow or a light radiation is then activated on the functionalised surface according to the procedure of the method of the invention previously disclosed so as to break the bonds with the agglomerates formed by the beads and by the particles of interest, the signal of the disturbance of the ion flow through pores 106 is recorded possibly amplified. As already mentioned, this procedure results especially convenient in the case in which the diameter of the pores is a lot longer than that of the particles and such as not to allow the direct reading of the passage of the particles therethrough. The count of the passage of the microbeads will be an index of the concentration of the particles of interest.

It should be noted that different sets of microbeads may be used, each functionalised for a different molecule of interest.

Figure 9:
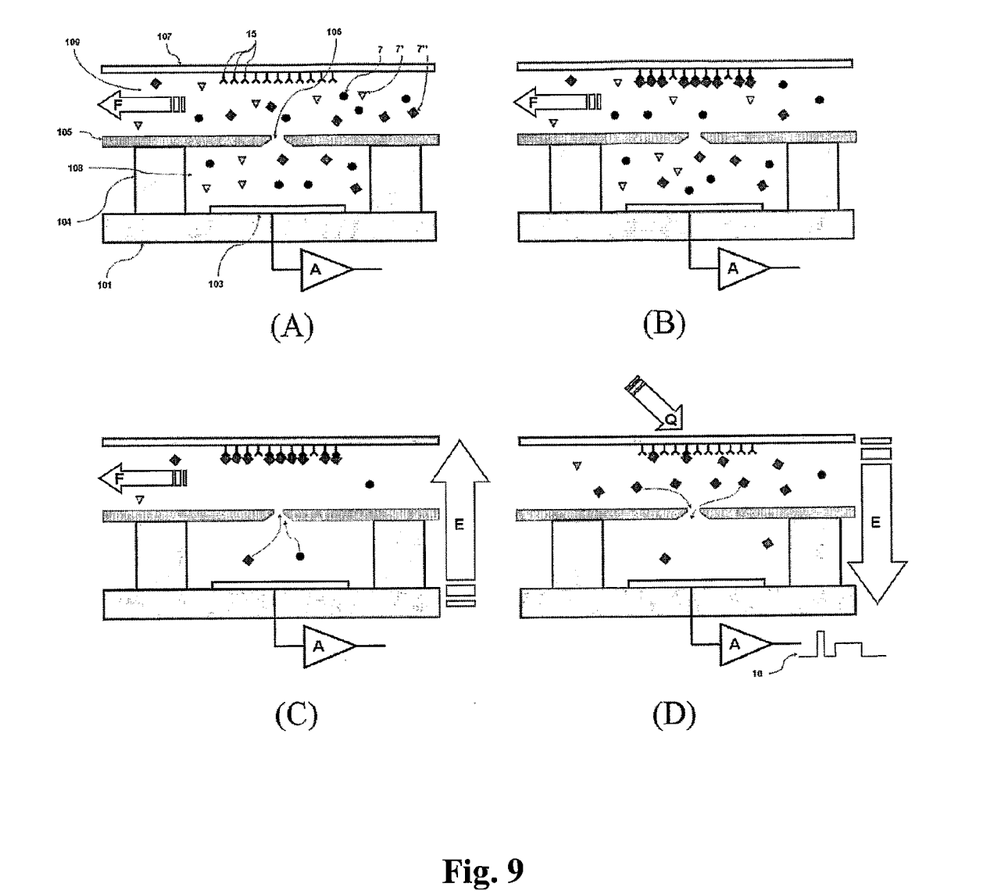
FIG. 9 shows consecutive steps of a further embodiment of the method according to the invention through corresponding detailed views of a section of the device of FIG. 5.

According to a further embodiment of the method of the invention, as shown in FIG. 9, the sample to be analysed is flowed in chamber 109, while the functionalisation for the particle of interest is obtained on surface 111 (it could be surface 111 of the lid, or that of electrode 107 obtained thereon, or also that of electrode 107' which extends on its entire surface) immediately overlaying cells 109. The continuous flow of sample F promotes the binding between receptor R and particle 7", whereas the various particles diffuse in a totally natural way through pores 106 also in underlying cells 108. At this point, as an optional and not strictly required step, to facilitate the discriminability of the single species, particle-free buffer may be flowed in chamber 109, possibly also activating an electric field to promote the outflow of the particles from chambers 108. Finally, by acting with a heat flow (Q) or with a light impulse (as previously disclosed) on lid 107 so as to break the bond between particles of interest and receptors and by applying a potential difference between the electrode of the lid and electrodes 103, it will be possible to trace back the concentration of particles of interest 7 by means of output signal 10 from amplifier A as already set forth. To facilitate (even if not strictly necessary if flow F is sufficiently weak) the discriminability of the particles, flow F may be interrupted during the latter step. As an alternative to the heat flow a buffer flow F may be used in overlaying chamber 109 with a gradient of pH with respect to the original one of the sample. The possibility of decreasing the bond energy by varying the pH of the solution is known.

The invention claimed is:

1. An apparatus (100) for counting particles (7, 7', 7") in a fluid comprising:
    a substrate (101) having a first surface (102);
    a lid (107) having a second surface (111) facing the first surface (102);
    at least one spacer element (103) interposed between the substrate (101) and the lid (107) so as to maintain the first and the second surface (102, 111) spaced from one another;
    a partition (105) with a plurality of through-openings (106) having nanometric size, the partition being interposed between said at least one spacer element (104) and said lid (107) so as to define at least one first chamber (109) between said partition and the lid and at least one second chamber (108) between said partition (105) and the substrate (101), the at least one first chamber and the at least one second chamber (108, 109) being fluidically connected to one another through at least one of said openings (106); the substrate (101) having at least one first electrode (103) on the first surface (102) and the lid (107) having a second electrode (107, 107'), the said at least one first electrode (103) being configured so as to detect an electric signal associated to the passage of one of said particles (7, 7', 7") through one said through-opening (106) of said partition (105),
    wherein:
    said at least one spacer element (104) comprises a peripheral element which defines laterally said at least one second chamber (108);
    said at least one spacer element (104) comprises a separator (114) to separate the at least one second chamber (108) in a plurality of microchambers (108'), each microchamber (108') being fluidically connected to the at least one first chamber (109) by at least one opening (106) of said partition (105);
    each microchamber (108') comprises a predetermined number of first electrodes (103) and a determined number of said openings, the number of said first electrodes (103) being greater than or equivalent to the number of said openings (106) included in said second chamber (108); and said at least one first electrode (103) is provided with at least one auxiliary focusing electrode (103') adapted to direct the particles of interest towards said opening (106) univocally associated to said first electrode (103).

2. The apparatus according to claim 1, characterised in that said at least one first electrode (103) is configured so as to detect said electrical magnitude by means of an electric connection to a respective amplifier (A), the signal detected by the respective said amplifier (A) being associable univocally to one said through-opening (106) of the partition (105).

3. The apparatus (100) according to claim 2, characterised in that said respective amplifier (A) connected to said at least one electrode (103) is incorporated into the substrate (101).

4. The apparatus (100) according to claim 1, comprising a plurality of first electrodes (103).

5. The apparatus (100) according to claim 4, characterised in that the number of said first electrodes (103) is greater or equivalent to the number of said openings (106).

6. The apparatus (100) according to claim 4, wherein said separator (114) consist of a grid (115), each mesh of which physically delimits each first electrode (103) from an adjacent first electrode, and each of the plurality of microchambers (108') comprises a single first electrode (103).

7. The apparatus (100) according to claim 4, characterised in that said separator (114) consist of a grid (115'), each mesh of which physically delimits a subset of said plurality of first electrodes (103) from adjacent first electrodes, and each of the plurality of microchambers (108') comprises a subset of said plurality of first electrodes.

8. The apparatus (100) according to claim 1, wherein said spacer element (104) is an integral part of the substrate or is fixed thereto.

9. The apparatus (100) according to claim 1, wherein, said partition (105) and the lid (107) are distinct elements which are stacked one on another in use.

10. The apparatus (100) according to claim 1, characterised in that said at least one first electrode (103) is arranged on said first surface (102) of the substrate (101) according to an array.

11. The apparatus (100) according to claim 1, characterised in that at least one of said first surface and said second surface (102, 103, 111) is functionalised so as to be suitable to establish in use a bond with said at least one particle of interest.

12. The apparatus (100) according to claim 1, characterised in that said at least one of first electrode (103) is functionalised so as to be suitable to establish in use a bond with said at least one particle of interest.

13. The apparatus (100) according to claim 1, characterised in that said second electrode (107, 107') is single and substantially extends on most part of the second surface (111).

14. A method for counting particles (7, 7', 7") of one or more species contained in a fluid, comprising:
    loading said fluid containing at least one of said particles (7, 7', 7") in at least one first microchamber (108, 109) defined between appropriately prearranged at least one first electrode (103, 107) and partition (105) with through-openings (106) having nanometric size;
    allowing the at least one particle to migrate from said first microchamber to a second chamber, the second chamber being defined between a second electrode (107, or 103) and said partition and being adjacent to the at least one first microchamber, through at least one opening (106) of the partition;
    detecting an electric signal associated to the passage of the at least one particle through said opening;
    processing said signal and correlating said signal to a property of said fluid;

identifying at least one particle of a species of interest (7") among said at least one particle (7, 7', 7") contained in the fluid with which the microchamber is loaded by constraining said at least one particle of the species of interest (7") to at least one surface (102, 103, 111) of said first and/or second chamber, said at least one surface (102 103, 111) being previously made suitable to establish in use a molecular bond specifically with particles of said species of interest;

separating particles of no interest (7, 7') present in said first chambers (109, 108) by flowing the particles of no interest away from the first microchamber; and applying a light radiation in order to break said molecular bond after separating the particles of no interest.

15. The method according to claim 14, further comprising univocally associating in use said at least one first electrode (103) to one said through-opening (106) of said partition (105).

16. The method according to claim 15, characterised in that said step of processing said detected signal comprises the step of associating said signal with said at least one opening (106) of the partition, said signal being physically associable to one or more electrodes associated to the opening (106) itself.

17. The method according to claim 15, characterised in that said step of detecting an electric signal is performed after the step of univocally associating in use said at least one first electrode (103) to one said through-opening (106) of said partition (105).

18. The method according to claim 14, characterised in that said property of the fluid is correlated to the number of said particles (7, 7', 7") contained in said fluid.

19. The method according to claim 14, characterised in that said step of allowing the at least one particle to migrate from said first microchamber (108, 109) to said second chamber (109, 108) is carried out by applying an electromagnetic force field by means of said at least one first electrode and said second electrode.

20. The method according to claim 14, characterised in that said step of detecting an electric signal is performed after the step of applying the light radiation.

\* \* \* \* \*